United States Patent [19]
Gibson et al.

[11] Patent Number: 5,629,444
[45] Date of Patent: May 13, 1997

[54] IMPROVED ACRYLONITRILE RECOVERY PROCESS

[75] Inventors: James S. Gibson, Lima; Jeffrey E. Rinker, Elida; Paul T. Wachtendorf, Wapakoneta; Sanjay P. Godbole, Solon, all of Ohio

[73] Assignee: The Standard Oil Company, Cleveland, Ohio

[21] Appl. No.: 659,480

[22] Filed: Jun. 6, 1996

[51] Int. Cl.$^6$ .................................................. C07C 253/18
[52] U.S. Cl. .......................................................... 558/466
[58] Field of Search ............................................. 558/466

[56] References Cited

U.S. PATENT DOCUMENTS 3,885,928  5/1975  Wu .
4,234,510  11/1980  Wu .

Primary Examiner—Johann Richter
Assistant Examiner—John Peabody
Attorney, Agent, or Firm—Michael F. Esposito; David J. Untener

[57] ABSTRACT

A process for the recovery of acrylonitrile or methacrylonitrile obtained from the reactor effluent of an ammoxidation reaction of propylene or isobutylene comprising passing the reactor effluent through an absorber column, a first decanter, recovery column, a second decanter and stripper column wherein the improvement comprises maintaining inside temperature of the first and second decanter at between about 32° F. to 75° F.

7 Claims, 1 Drawing Sheet

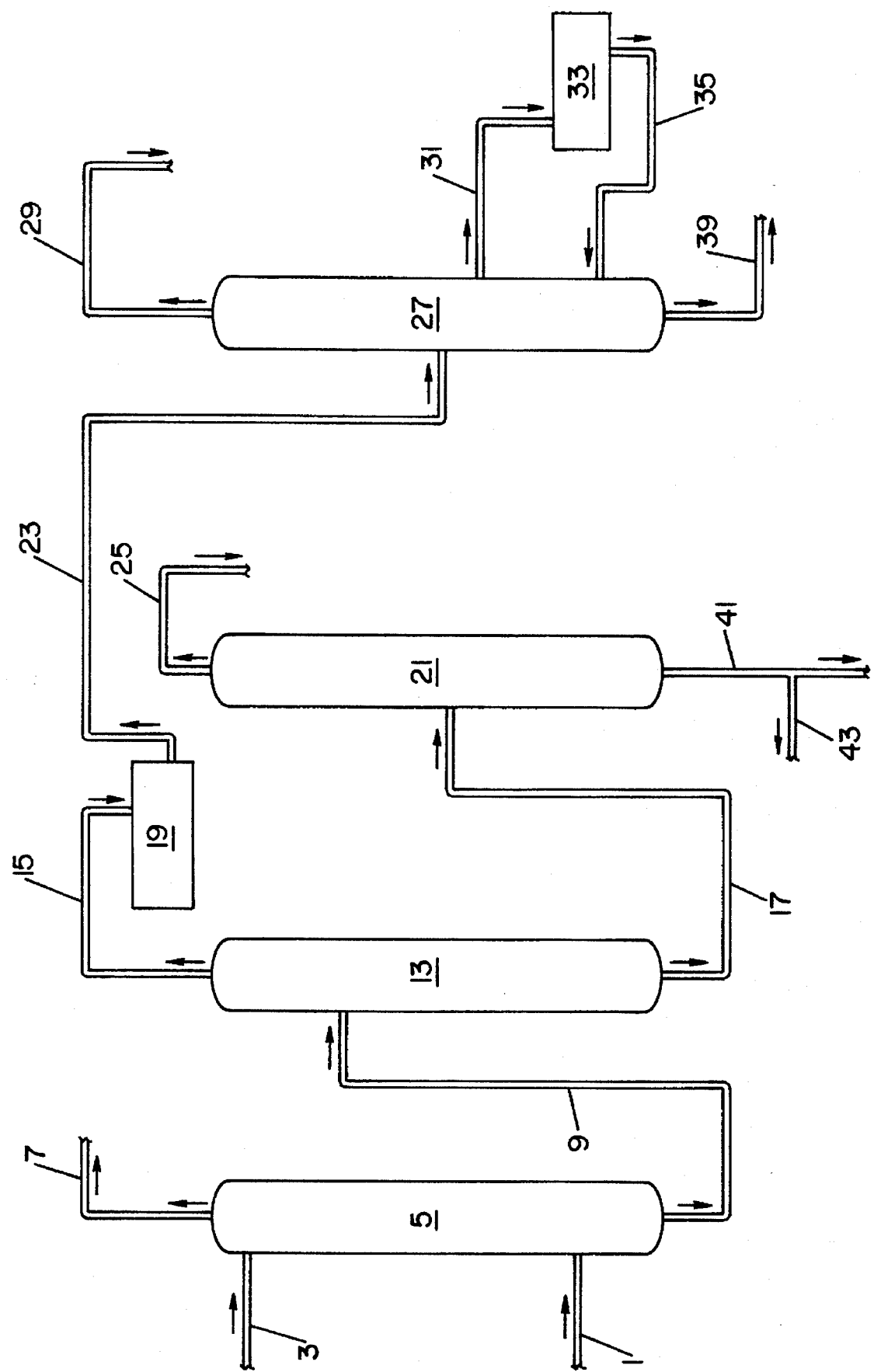

IMPROVED ACRYLONITRILE RECOVERY PROCESS

BACKGROUND OF THE INVENTION

FIELD OF THE INVENTION

The present invention is directed to an improved process for the manufacture of acrylonitrile or methacrylonitrile. In particular, the present invention is directed to the improvement in the recovery procedures utilized during the manufacture of acrylonitrile or methacrylonitrile. In addition, the improved process of the present invention improves the quality of the resulting product by minimizing peroxide impurities.

Recovery of acrylonitrile/methacrylonitrile produced by the ammoxidation of propylene or isobutylene on a commercial scale has been accomplished by quenching the reactor effluent with water followed by passing the gaseous stream containing acrylonitrile or methacrylonitrile resulting from the quench to an absorber where water and the gases are contacted in counter-current flow to remove substantially all the acrylonitrile or methacrylonitrile, the aqueous stream containing substantially all the acrylonitrile or methacrylonitrile is then passed through a series of distillation columns and associated decanters for separation and purification of product acrylonitrile or methacrylonitrile.

Typical recovery and purification systems that are used during the manufacture of acrylonitrile or methacrylonitrile are disclosed in U.S. Pat. Nos. 4,234,510 and 3,885,928, assigned to the assignee of the present invention and herein incorporated by reference.

SUMMARY OF THE INVENTION

It is the primary object of the present invention to provide an improved process for the manufacture of acrylonitrile or methacrylonitrile.

It is another object of the present invention to provide an improved recovery and purification procedure during the manufacture of acrylonitrile or methacrylonitrile.

It is a further object of the present invention to provide an improved process for the manufacture of acrylonitrile or methacrylonitrile which reduces the amount of impurities in the resultant final product.

Additional objects, advantages and novel features of the invention will be set forth in part in the description which follows, and in part, will become apparent to those skilled in the art upon examination of the following or may be learned by the practice of the invention. The objects and advantages of the invention may be realized and obtained by means of the instrumentalities and combinations particularly pointed out in the appended claims.

To achieve the foregoing and other objects and in accordance with the purpose of the present invention as embodied and broadly described herein, the process of the present invention comprises transporting the reactor effluent obtained during the ammoxidation of propylene or isobutylene to a quench column wherein the hot effluent gases are cooled by contact with an aqueous spray, passing the cooled reactor effluent overhead to an absorber column wherein the crude acrylonitrile or methacrylonitrile is absorbed in water, passing the aqueous solution containing the acrylonitrile or methacrylonitrile to a first decanter where a first aqueous layer and a first organic layer containing acryonitrile and methacrylonitrile are formed, transferring the first organic layer to a second decanter where a second water layer and second organic layer are formed, and recovering the acrylonitrile or methacrylonitrile from the second organic layer wherein the improvement comprises maintaining the first and second decanter at a temperature of about 32° F. to about 75° F. and maintaining the second decanter at a temperature of about 32° F. to about 75° F. Preferably the temperature of the first decanter is maintained at about 32° F. to 70° F. especially preferred being 32° F. to 65° F. Preferably, the temperature of the second decanter is maintained at between about 35 to 68° F., especially preferred being 40° to 65° F.

In a preferred embodiment of the present invention, the process is performed with the reactor effluent obtained from the ammoxidation of propylene, ammonia and oxygen to produce acrylonitrile.

In a still preferred embodiment of the present invention, the reactor effluent is obtained by the reaction of propylene, ammonia and air in a fluid bed reactor while in contact with a fluid bed catalyst.

Conventional fluid bed ammoxidation catalyst may be utilized in the practice of the invention. For example, fluid bed catalyst as described in U.S. Pat. Nos. 3,642,930 and 5,093,299, herein incorporated by reference, may be utilized in the practice of the present invention.

The present invention allows for the more efficient operation during the recovery and purification of the product acrylonitrile or methacrylonitrile. The operation of the decanters within the temperature range set forth above results in improved water phase separation thereby increasing the water phase volume in the decanters. This improved separation means that higher volumes of product can be treated during subsequent recovery and purification steps (i.e. distillation and drying) without any increase in the size of any. equipment. Another advantage of the practice of the invention is that operation of the decanter in the temperature range set forth above leads to minimization of the water soluble impurities such as peroxide which are detrimental to end product users.

BRIEF DESCRIPTION OF THE DRAWING

FIG. 1 is a schematic representation of the process as it applies to the manufacture of acrylonitrile.

DETAILED DESCRIPTION OF THE INVENTION

The present invention will now be described in detail with reference to the FIGURE. The reactor effluent obtained by the ammoxidation of propylene or isobutylene, ammonia and oxygen containing gas in a fluid bed reactor (not shown) while in contact with a fluid bed ammoxidation catalyst is transported to a quench column (not shown) wherein the hot effluent gases are cooled by contact with water spray. Typically, any excess ammonia contained in the effluent is neutralized by contact with sulfuric acid in the quench to remove the ammonia as ammonium sulfate. The cooled effluent gas containing the desired product (acrylonitrile or methacrylonitrile, acetonitrile and HCN) is then passed into the bottom of an absorber column 5 via line 1 wherein the products are absorbed in water which enters absorber column 5 from the top via line 3. The non-absorbed gases pass from the absorber through pipe 7 located at the top of the absorber 5. The aqueous stream containing the desired product is then passed via line 9 from the bottom of absorber 5 to the upper portion of a first distillation column 13 (recovery column) for further product purification. The product is recovered from the top portion of recovery column 13 and sent to decanter 19 via line 15. The aqueous solution containing crude acrylonitrile is allowed to separate into first layer comprising water and a second layer comprising organic product (e.g. crude acrylonitrile and HCN) in decanter 19. The product layer is then transferred via line 23 to a second distillation column 27 for further purification and recovery of product acrylonitrile or methacrylonitrile. The bottom stream obtained from column 13 may be sent directly to an incinerator or to a stripper distillation column 21 via line 17 to recover crude acetonitrile as an overhead via line 25. The bottom stream obtained from column 21 may be sent to an incinerator via lines 41 and 43.

The product stream entering distillation column 27 is distilled and product acrylonitrile is recovered as a side stream from column 27 via line 31. This acrylonitrile product is stored in a second decanter 33 which is maintained at a temperature of between about 32° F. to 70° F. until a second phase separation of product acrylonitrile and water has taken place. The product acrylonitrile is then removed from decanter 33 via line 35 and introduced into the bottom of column 27 for exit via line 39 for final purification and recovery. Coproduct HCN is recovered from column 27 as an overhead stream via line 29 and either incinerated or purified and recovered by conventional means known in the art.

Preferably, the ammoxidation reaction is performed in a fluid bed reactor although other types of reactors such as transport line reactors are envisioned. Fluid bed reactors, for the manufacture of acrylonitrile are well known in the prior art. For example, the reactor design set forth in U.S. Pat. No. 3,230,246, herein incorporated by reference, is suitable.

Conditions for the ammoxidation reaction to occur are also well known in the prior art as evidenced by U.S. Pat. Nos. 5,093,299; 4,863,891; 4,767,878 and 4,503,001; herein incorporated by reference. Typically, the ammoxidation process is performed by contacting propylene or isobutylene in the presence of ammonia and oxygen with a fluid bed catalyst at an elevated temperature to produce the acrylonitrile or methacrylonitrile. Any source of oxygen may be employed. For economic reasons, however, it is preferred to use air. The typical molar ratio of the oxygen to olefin in the feed should range from 0.5:1 to 4:1, preferably from 1:1 to 3:1. The molar ratio of ammonia to olefin in the feed in the reaction may vary from between 0.5:1 to 5:1. There is really no upper limit for the ammonia-olefin ratio, but there is generally no reason to exceed a ratio of 5:1 for economic reasons.

The reaction is carried out at a temperature of between the ranges of about 260° to 600° C., but the preferred ranges being 310° to 500° C., especially preferred being 350° to 480° C. The contact time, although not critical, is generally in the range of 0.1 to 50 seconds, with preference being to a contact time of 1 to 15 seconds.

In addition to the catalyst of U.S. Pat. No. 3,642,930, other catalysts suitable for the practice of the present invention are set forth in U.S. Pat. No. 5,093,299, herein incorporated by reference.

The conditions under which the absorber column, recovery column and stripper column are maintained range between 5 to 7 psig (80° F. to 110° F.), 1 to 4.5 psig (155° F. to 170° F.), and 7 to 13 psig (170° F. to 210° F.), respectively.

The present invention not only results in an unexpected improvement in the production rates but achieves this improvement without increasing the size of the columns utilized in the recovery and purification section. In addition, the attendant increase in production rates does not come with any observed deterioration in the product quality. In fact, product quality improves with the practice of the present invention due to the lowering of the impurity levels of peroxide found in the final product.

As will be evident to those skilled in the art, various modifications of this invention can be made or followed in light of the foregoing disclosure and discussion without departing from the spirit and scope of the disclosure or from the scope of the claims.

What is claimed is:

1. A process for the manufacture of acrylonitrile or methacrylonitrile comprising transporting the reactor effluent obtained during the ammoxidation of propylene or isobutylene to a quench column wherein the hot effluent gases are cooled by contact with an aqueous spray, passing the cooled reactor effluent overhead to an absorber column wherein the crude acrylonitrile or methacrylonitrile is absorbed in water, passing the aqueous solution containing the crude acrylonitrile or methacrylonitrile to a first decanter where a first aqueous layer and a first organic layer containing acrylonitrile and methacrylonitrile are formed, transferring the first organic layer to a second decanter where a second water layer and second organic layer are formed, and recovering the acrylonitrile or methacrylonitrile from the second organic layer wherein the improvement comprises maintaining the first and second decanter at an inside temperature of about 32° F. to about 75° F.

2. The process of claim 1 wherein the inside temperature of the first decanter is maintained at about 32° F. to 70° F.

3. The process of claim 2 wherein the inside temperature of the first decanter is maintained at between 32° F. to 65° F.

4. The process of claim 1 wherein the inside temperature of the second decanter is maintained at between about 35 to 68° F.

5. The process of claim 4 wherein the inside temperature of the second decanter is between about 40° to 65° F.

6. The process of claim 1 wherein the reactor effluent is obtained from the ammoxidation of propylene, ammonia and oxygen to produce acrylonitrile.

7. The process of claim 1 wherein the reactor effluent is obtained by the reaction of propylene, ammonia and air in a fluid bed reactor while in contact with a fluid bed catalyst.

\* \* \* \* \*